United States Patent
Turunen et al.

(10) Patent No.: US 11,267,837 B2
(45) Date of Patent: Mar. 8, 2022

(54) METHOD AND AN APPARATUS FOR WASHING A CRUDE LIGNIN, A SOLUBLE CARBOHYDRATE CONTAINING FRACTION, A SOLID FRACTION AND THEIR USE

(71) Applicant: UPM-KYMMENE CORPORATION, Helsinki (FI)

(72) Inventors: Sami Turunen, Lappeenranta (FI); Juha Tamper, Levänen (FI)

(73) Assignee: UPM-KYMMENE CORPORATION, Helsinki (FI)

(*) Notice: Subject to any disclaimer, the term of this patent is extended or adjusted under 35 U.S.C. 154(b) by 22 days.

(21) Appl. No.: 15/577,481

(22) PCT Filed: May 26, 2016

(86) PCT No.: PCT/FI2016/050363
§ 371 (c)(1),
(2) Date: Nov. 28, 2017

(87) PCT Pub. No.: WO2016/193536
PCT Pub. Date: Dec. 8, 2016

(65) Prior Publication Data
US 2018/0148467 A1    May 31, 2018

(30) Foreign Application Priority Data
May 29, 2015 (FI) ...................................... 20155413

(51) Int. Cl.
*C07G 1/00* (2011.01)
*B01D 12/00* (2006.01)
(Continued)

(52) U.S. Cl.
CPC ............... *C07G 1/00* (2013.01); *B01D 12/00* (2013.01); *B01D 33/04* (2013.01); *B01D 33/64* (2013.01); *C07H 1/08* (2013.01)

(58) Field of Classification Search
CPC ... C07G 1/00; C08H 6/00; C08H 8/00; B01D 12/00; B01D 33/04
See application file for complete search history.

(56) References Cited

U.S. PATENT DOCUMENTS 4,046,621 A    9/1977    Sexton
4,539,827 A    9/1985    Klein
(Continued)

FOREIGN PATENT DOCUMENTS

CN    101952504 A    1/2011
CN    103429642 A    12/2013
(Continued)

OTHER PUBLICATIONS

George G. Chase & Ernest Mayer, "Filtration," in 11 Kirk-Othmer Encyclopedia of Chemical Technology 321 (published online Mar. 14, 2003), https://onlinelibrary.wiley.com/doi/pdf/10.1002/0471238961.0609122019220118.a01 pub2.*

(Continued)

*Primary Examiner* — Nicholas E Hill
(74) *Attorney, Agent, or Firm* — Nixon Peabody LLP

(57) ABSTRACT

The invention relates to a method and an apparatus for washing a crude lignin slurry (5) formed from plant based raw material, wherein the method comprises separating a soluble carbohydrate containing fraction (10) from the crude lignin slurry (5) by using displacement washing in at least one solid-liquid separation stage (6) so that the crude lignin slurry is prepressed, washed and pressed, and recovering a solid fraction (11) and the soluble carbohydrate containing fraction (10). Further, the invention relates to the soluble carbohydrate containing fraction and the solid fraction, and their uses.

17 Claims, 4 Drawing Sheets

(51) Int. Cl.
   *B01D 33/04* (2006.01)
   *B01D 33/64* (2006.01)
   *C07H 1/08* (2006.01)

(56) References Cited

U.S. PATENT DOCUMENTS

| | | | |
|---|---|---|---|
| 4,915,830 | A | 4/1990 | Mackay et al. |
| 5,238,501 | A | 8/1993 | Kappel et al. |
| 8,486,224 | B2 | 7/2013 | Öhman |
| 2007/0259412 | A1* | 11/2007 | Belanger ............ D21C 5/00 435/161 |
| 2008/0047674 | A1 | 2/2008 | Ohman et al. |
| 2010/0325947 | A1* | 12/2010 | Ohman ............... C08H 8/00 44/606 |
| 2013/0213550 | A1* | 8/2013 | Berlin ............... B29C 70/34 156/62.2 |
| 2013/0331555 | A1* | 12/2013 | Malkki ............... C07G 1/00 530/502 |
| 2015/0128933 | A1 | 5/2015 | Larsen |
| 2018/0162891 | A1 | 6/2018 | Miettinen |
| 2018/0265938 | A1* | 9/2018 | Miettinen ........... C12P 19/02 |

FOREIGN PATENT DOCUMENTS

| | | |
|---|---|---|
| EA | 200701702 A1 | 12/2007 |
| JP | H 11-506934 A | 6/1999 |
| JP | 2006-068659 A | 3/2006 |
| JP | 2008-513549 A | 5/2008 |
| JP | 2012-170845 A | 9/2012 |
| JP | 2018-516292 A | 6/2018 |
| RU | 2508301 C1 | 2/2014 |
| WO | 2006/031175 A1 | 3/2006 |
| WO | 2008/079072 A1 | 7/2008 |
| WO | 2009/104995 A1 | 8/2009 |
| WO | 2011/039635 A2 | 4/2011 |
| WO | 2012/162443 A2 | 11/2012 |
| WO | 2013/083876 A2 | 6/2013 |
| WO | 2012/120184 A2 | 9/2013 |
| WO | WO 2016/124821 | 8/2016 |
| WO | WO 2016/124821 A1 | 8/2016 |
| WO | WO 2016/124822 | 8/2016 |

OTHER PUBLICATIONS

Bodo Saake & Ralph Lehnen, "Lignin," in 21 Ullmann's Encyclopedia of Industrial Chemistry 21, published online 2007.*

International Search Report from International Application No. PCT/FI2016/050363 dated Aug. 12, 2016.

Search Report from Finnish Application No. 20155413 dated Jan. 7, 2016.

Office Action from Finnish Application No. 20155413 dated Jun. 22, 2017.

International Search Report in Russian Application No. 20155413, dated Jun. 6, 2019 (4 pages, w/ English translation).

Takeyama, E. et al., "Dietary Fiber in Soybeans and Processed Soybean Foods," Journal of Food Science and Technology, vol. 33, No. 4, pp. 263-269 (1986).

Sievers, D.A. et al., "A low-cost solid-liquid separation process for enzymatieally hydrolyzed corn stover slurries," Bioresource Technology, 187, (Epub Mar. 25, 2015) pp. 37-42.

Japanese Office Action in Japanese Patent Application No. JP 2017-559681, dated Mar. 10, 2020 (6 pages). (with English translation)

Australian Office Action in Australian Patent Application No. AU 2016272205, dated Jul. 28, 2020 (5 pages).

New Zealand Office Examination Report in New Zealand Patent Application No. 738011, dated Jul. 1, 2021 (6 pages).

* cited by examiner

METHOD AND AN APPARATUS FOR WASHING A CRUDE LIGNIN, A SOLUBLE CARBOHYDRATE CONTAINING FRACTION, A SOLID FRACTION AND THEIR USE

CROSS-REFERENCE TO RELATED APPLICATIONS

This application is a U.S. National Stage Application of International Application No. PCT/FI2016/050363, filed on May 26, 2016, which claims priority to Finnish Patent Application No. 20155413, filed on May 29, 2015, both of which are incorporated by reference herein in their entireties.

FIELD OF THE INVENTION

The invention relates to a method and an apparatus for washing crude lignin slurry. Further, the invention relates to a soluble carbohydrate containing fraction and its use. Further, the invention relates to a solid fraction and its use.

BACKGROUND OF THE INVENTION

Known from prior art is different methods for forming carbohydrates and lignin from different raw materials, such as biomass. Many bio-refinery processes, e.g. hydrolysis, generate lignin and sugars after the treatment of the biomass.

OBJECTIVE OF THE INVENTION

The objective of the invention is to disclose a new method for washing crude lignin slurry. Another objective of the invention is to purify the crude lignin and to form a purified lignin fraction. Another objective of the invention is to produce a soluble carbohydrate containing fraction. Another objective of the invention is to improve fractionation of biomass for producing a soluble material free solid fraction and a soluble carbohydrate containing fraction.

SUMMARY OF THE INVENTION

The method for washing crude lignin slurry formed from plant based raw material is characterized by separating a soluble carbohydrate containing fraction from the crude lignin slurry by using displacement washing in at least one solid-liquid separation stage so that the crude lignin slurry is prepressed, washed and pressed, and recovering a solid fraction and the soluble carbohydrate containing fraction.

The apparatuses for washing a crude lignin slurry formed from plant based raw material are characterized by: (1) at least one solid-liquid separation device in which a soluble carbohydrate containing fraction is separated from the crude lignin slurry by using displacement washing and in which the crude lignin slurry is prepressed, washed and pressed, at least one feeding device for feeding the crude lignin slurry into the separation device, and a supplying device for supplying a solid fraction and the soluble carbohydrate containing fraction out from the separation device; (2) at least one belt filtration device in which a soluble carbohydrate containing fraction is separated from the crude lignin slurry by filtration and washing, at least one feeding device for feeding the crude lignin slurry into the belt filtration device, and a supplying device for supplying a solid fraction and the soluble carbohydrate containing fraction out from the belt filtration device; and (3) at least one solid-liquid separation device in which a soluble carbohydrate containing fraction is separated from the crude lignin slurry by at least two pressing steps and the crude lignin slurry is diluted between two pressing steps, at least one feeding device for feeding the crude lignin slurry into the separation device, and a supplying device for supplying a solid fraction and the soluble carbohydrate containing fraction out from the separation device.

The soluble carbohydrate containing fraction obtainable by separating a soluble carbohydrate containing fraction from the crude lignin slurry by using displacement washing in at least one solid-liquid separation stage so that the crude lignin slurry is prepressed, washed and pressed, and recovering a solid fraction and the soluble carbohydrate containing fraction.

The solid fraction obtainable by separating a soluble carbohydrate containing fraction from the crude lignin slurry by using displacement washing in at least one solid-liquid separation stage so that the crude lignin slurry is prepressed, washed and pressed, and recovering a solid fraction and the soluble carbohydrate containing fraction.

The use of the soluble carbohydrate containing fraction obtainable by separating a soluble carbohydrate containing fraction from the crude lignin slurry by using displacement washing in at least one solid-liquid separation stage so that the crude lignin slurry is prepressed, washed and pressed, and recovering a solid fraction and the soluble carbohydrate containing fraction, wherein the soluble carbohydrate containing fraction is used as a source material in fermentation, hydrolysis, catalytic process, polymerization process, enzymatic process, manufacture of binder, manufacture of feed, manufacture of food or their combination.

The use of the solid fraction obtainable by separating a soluble carbohydrate containing fraction from the crude lignin slurry by using displacement washing in at least one solid-liquid separation stage so that the crude lignin slurry is prepressed, washed and pressed, and recovering a solid fraction and the soluble carbohydrate containing fraction, wherein the solid fraction is used as a source material in hydrolysis, polymerization process, manufacture of a composite material, manufacture of binder, manufacture of feed, manufacture of food, combustion process or their combination.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION OF THE INVENTION

Figure 1:
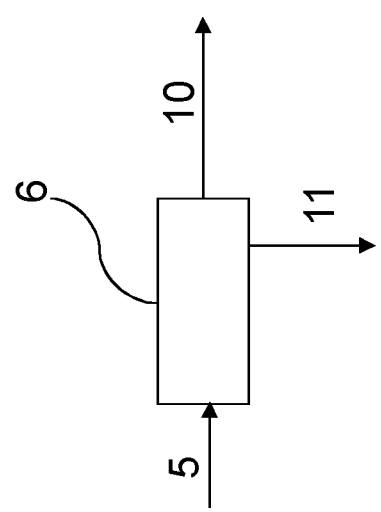
FIG. 1 is a flow chart illustration of a method according to one embodiment of the present invention.

The invention relates to a method for washing crude lignin slurry (5) formed from plant based raw material (1).

In the method of the present invention, the method comprises separating a soluble carbohydrate containing fraction (10) from the crude lignin slurry (5) by using displacement washing in at least one solid-liquid separation stage (6) so that the crude lignin slurry (5) is prepressed, washed and pressed, and recovering a solid fraction (11) and the soluble carbohydrate containing fraction (10). The separation stage (6) comprises one or more separation steps.

Figure 2:
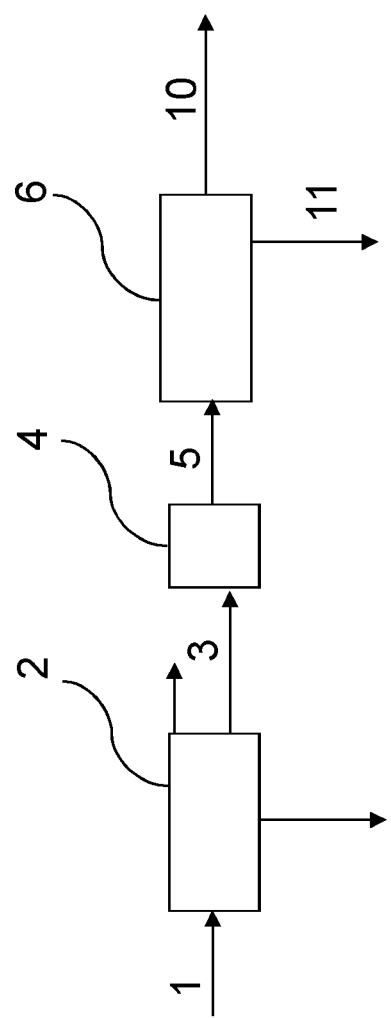
FIG. 2 is a flow chart illustration of a method according to another embodiment of the present invention.

One embodiment of the method of the present invention is shown in FIG. 1. Another embodiment of the method of the present invention is shown in FIG. 2.

The apparatus of the present invention comprises at least one solid-liquid separation device (6) into which crude lignin slurry (5) formed from plant based raw material (1) is conducted and in which a soluble carbohydrate containing fraction (10) is separated from the crude lignin slurry (5) by using displacement washing and in which the crude lignin slurry is prepressed, washed and pressed. Further, the apparatus comprises at least one feeding device, such as a pump, for feeding the crude lignin slurry (5) into the separation device. Further, the apparatus comprises means, such as discharge means or outlet means, for supplying a solid fraction (11) and the soluble carbohydrate containing fraction (10) out from the separation device.

The apparatus of the present invention comprises at least one solid-liquid separation device in which a soluble carbohydrate containing fraction (10) is separated from the crude lignin slurry (5) by at least two pressing steps and the crude lignin slurry is diluted between two pressing steps, and at least one feeding device for feeding the crude lignin slurry (5) into the separation device, and means for supplying a solid fraction (11) and the soluble carbohydrate containing fraction (10) out from the separation device.

The apparatus of the present invention comprises at least one belt filtration device as a solid-liquid separation device in which a soluble carbohydrate containing fraction (10) is separated from the crude lignin slurry (5) by filtration and washing. Further, the apparatus comprises at least one feeding device for feeding the crude lignin slurry (5) into the belt filtration device, and means for supplying a solid fraction (11) and the soluble carbohydrate containing fraction (10) out from the belt filtration device.

The invention is based on washing a crude lignin material. Further, the invention is based on a solid-liquid separation. Simultaneously, more pure solid lignin fraction comprising solids can be formed. The purity of the solid lignin fraction can be increased by means of the present invention. In one embodiment, a replacement washing is used which increases purity of the solid fraction. In one embodiment, small amount of washing water is used. Further, if the washing water is recovered so it can be utilized in the process or products. Further, soluble carbohydrates can be recovered and utilized in final products.

In this context, a soluble carbohydrate containing fraction (10) means a soluble carbohydrate containing filtrate which is separated from the crude lignin slurry. In a preferred embodiment, the soluble carbohydrate containing fraction includes carbohydrates, preferably C6 sugars ($C_6H_{12}O_6$ or $(C_6(H_2O)_n)$). The soluble carbohydrate containing fraction may comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or $(C_5H_8O_4)_n$). Preferably, the soluble carbohydrate containing fraction comprises soluble C6 carbohydrates ($C_6H_{12}O_6$ or $C_6(H_2O)_n$) and other soluble carbohydrates. The soluble carbohydrate containing fraction may comprise also other components.

In this context, a solid fraction (11) means a solid residue, such as a solid cake, when the soluble carbohydrate containing filtrate has been separated. In a preferred embodiment, the solid fraction comprises lignin and carbohydrates, preferably solid C6 carbohydrates ($C_6H_{12}O_6$ or $C_6(H_2O)_n$). The solid fraction may comprise also other carbohydrates and other components. Preferably, the solid fraction is in the solid form.

In this context, plant based raw material (1) means any plant based raw material, e.g. wood based material. The plant based raw material includes lignin, cellulose and hemicellulose. In one embodiment, the plant based raw material is selected from the group consisting of wood based material, wood, lignocellulose biomass, agricultural residues, bagasse based material, sugarcane bagasse, corn based material, corn stover, wheat straw, rice straw, woody biomass, woody perennials, vascular plants and the like and their mixtures and their combinations. In one embodiment, the plant based raw material is wood based material or a mixture comprising wood based material. In one embodiment, the plant based raw material comprises plant pieces, e.g. wood pieces.

In this context, crude lignin slurry (5) means any crude lignin containing composition that is in the form a slurry. The slurry contains solid material and liquid, e.g. water. Preferably, the slurry can be pumped. Preferably, the slurry contains free liquid, such as free water. Preferably, the crude lignin slurry has been formed from the lignocellulose material (3), in one embodiment from solid component or solid components from the lignocellulose material (3). The lignocellulose material (3) has been formed by treating, e.g. by pre-treating, the plant based raw material by means of at least one suitable treatment method in one or more steps. In one embodiment, the lignocellulose material (3) is formed from the plant based raw material (1) and is treated in one or more treatment step (2) by treatment, e.g by pretreatment, selected from the group consisting of physical treatment, such as milling, extrusion, microwave treatment, ultrasound treatment and freeze treatment, chemical treatment, such as acid treatment, alkaline treatment, ionic liquid treatment, organosolv treatment and ozonolysis, physico-chemical treatment, such as steam explosion treatment, ammonia fiber explosion treatment, $CO_2$ explosion treatment, liquid hot water treatment and wet oxidation, biological treatment and their combinations. Preferably, the plant based raw material is treated to dissolve hemicellulose. In one embodiment, the lignocellulose material is formed or treated by the hydrolysis, e.g. acid hydrolysis, autohydrolysis, thermal hydrolysis, enzymatic hydrolysis, supercritical hydrolysis and/or subcritical hydrolysis, in which at least a part of lignin is separated from the raw material in connection with the hydrolysis. In one embodiment, the lignocellulose material is formed or treated by the steam explosion, in which hemicelluloses are treated and in which at least a part of polysaccharides of the hemicelluloses degrade into monosaccharides and oligosaccharides. In one embodiment, the lignocellulose material is formed or treated by the hydrolysis and by the steam explosion in one or more steps. In one embodiment, the lignocellulose material is formed or treated by the catalytic pretreatment, e.g. by using acid or base as catalyst. In the pretreatment process the plant based raw material (1) enters the reactor unit where the pretreatment takes place. In one embodiment, the treated lignocellulose material (3) can be introduced a separation in which soluble components and solid material of the lignocellulose material are separated. In one embodiment, the lignocellulose material (3) is used as such, without the separation of soluble components, as the lignocellulose material. In one embodiment, the lignocellulose material (3) is further processed by means of suitable treatment (4), e.g. by means of a cellulose hydrolysis in which cellulose is hydrolyzed. In one embodiment, the lignocellulose material (3) is processed by means of an enzymatic treatment or an acid treatment or other suitable treatment in order to form crude lignin. In one embodiment, the enzymatic treatment is an enzymatic hydrolysis. In one embodiment, the acid treatment is an acid hydrolysis. In one embodiment, said other treatment is a supercritical or subcritical hydrolysis.

Preferably, the crude lignin is in the form of slurry after the treatment. In one embodiment, the crude lignin slurry (5) has been processed by means of a cellulose hydrolysis (4), e.g. by means of an enzymatic treatment or an acid treatment or other suitable treatment. Further, in one embodiment, the formed crude lignin slurry can be dewatered, e.g. by dewatering presses in two stages.

In one embodiment, the crude lignin slurry (5) contains lignin and carbohydrates. Preferably, the carbohydrates have $C_n(H_2O)_n$ or $C_n(H_2O)_{n-}$. Preferably, the crude lignin slurry includes carbohydrates, such as soluble C6 carbohydrates and solid C6 carbohydrates ($C_6H_{12}O_6$ or $C_6(H_2O)_n$). The carbohydrates can comprise monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or $(C_5H_8O_4)_n$). In one embodiment, the crude lignin slurry comprises at least monosaccharides. The crude lignin slurry may contain one or more material components. Preferably, the crude lignin slurry comprises solid components. In one embodiment, the crude lignin slurry is in the form of suspension which contains liquid, such as water.

In one embodiment, the lignocellulose material (3) consists of fine solid particles. By means of the fine particle size high yields and low amount of degradation may be achieved in the process. Preferably, fine solid particles are fiber-like or indefinable particles smaller than 0.2 mm, or they are particles that are small enough to pass through the Bauer McNett 200-mesh screen. The pretreatment and treatment processes decrease the particle size and fibre length of original wood fibre, which can be defined by separating fibres by cooking the wood in e.g. sulphate process or maceration. The sulphate process is resulting fibre length of about 80% of the one after the maceration.

Particle size of the solid particles and the lignocellulose material can be defined or measured, e.g. with an optical measurement device, such as Metso FS5, or with a laser diffraction method, such as Coulter LS230. The values for particle size are depending on the method and thus values from Metso FS5 and Coulter LS230 cannot be directly compared. In one embodiment, particle size of the solid particles can be defined based on ISO 16065-N or TAPPI T271.

Fibre length of the solid particles can be defined based on ISO 16065-N, when fibres are defined as material longer than 0.2 mm. Fibre length of the solid particles can be defined based on TAPPI T271, when fibre length is 0.01 to 7.60 mm. In connection with Metso FS5, Lc means contour length, i.e. centerline fiber length, which is fiber length measured from the fibers center line from one end to another.

Length-weighted Lc(l) means length-weighted fiber length which is average fiber length measured from a fiber distribution weighted according to the TAPPI T271 standards. Weight-weighted Lc(w) means weight-weighted fiber length which is likewise average fiber length measured from a fiber distribution weighted according to the TAPPI T271 standards. Arithmetic Lc(n) means arithmetic mean which is calculated from the population distribution of fibers. In this result average length is calculated from the length distribution. F1(1)% means length weighted distribution % (width>10 µm, length<0.2 mm). Fiber width is measured as integral value from the middle of the fiber to account for tapered ends.

In one embodiment, length-weighted particle length Lc(l) of the lignocellulose material (3) is below [(0.4)×(corresponding unrefined sulphate pulp fibre length)], preferably below [(0.3)×(corresponding unrefined sulphate pulp fibre length)], more preferable below [(0.2)×(corresponding unrefined sulphate pulp fibre length)], most preferable below [(0.1)×(corresponding unrefined sulphate pulp fibre length)].

In one embodiment, fine particle width (fraction 0-0.2 mm) of the lignocellulose material (3) is below [(0.7)×(corresponding unrefined sulphate pulp fibre length)], preferably below [(0.6)×(corresponding unrefined sulphate pulp fibre length)], more preferable below [(0.5)×(corresponding unrefined sulphate pulp fibre length)], most preferable below [(0.4)×(corresponding unrefined sulphate pulp fibre length)].

In one embodiment, the solid fraction of the lignocellulose material (3) comprises fine solid particles which are fiber-like or indefinable particles with longest dimension shorter than 0.2 mm measured with optical Metso FS5 (fraction F1(l) of length weighted Lc(l) measurements and calculations). In one embodiment, the solid fraction of hardwood comprises particles with longest dimension shorter than 0.2 mm over 70% (F1(l)>70%), preferably over 80%, more preferably over 90% and most preferably over 98% by weight, defined by Metso FS5. In one embodiment, the solid fraction of softwood comprises particles with longest dimension shorter than 0.2 mm over 50% (F1(l)>50%), preferably over 60%, more preferably over 70% and most preferably over 80% by weight, defined by Metso FS5.

In one embodiment, the solid fraction of the lignocellulose material (3) comprises fine solid particles which are fiber-like or indefinable particles.

The length weighted length Lc(l) of solid fraction is measured based TAPPI T271 standard includes all the particles detected and filling the requirements of measurement. TAPPI T271 defines fiber length of material to have longest dimension from 0.01 to 7.60 mm.

In one embodiment, the solid fraction of the lignocellulose material (3) comprises fine solid particles which are fiber-like or indefinable particles.

The length weighted length Lc(l) of solid fraction is measured with Metso FS5. The length weighted Lc(l)-value is 40% or less of the length of corresponding unrefined sulphate pulp fibre length, preferably 30% or less, more preferably 20% or less, most preferably 10% or less. And the width of the fine particle fraction of length weighted particles (Lc(l)fraction 0-0.2 mm) is 70% or less of width of the corresponding sulphate pulp fibre, preferably 60% or less, more preferably 50% or less, the most preferably 40% or less.

In one embodiment, the solid fraction of hardwood of the lignocellulose material (3) comprises fine solid particles which are fiber-like or indefinable particles. The length weighted length Lc(l) of solid fraction is measured with Metso FS5. The length weighted Lc(l)fractions over 0.2 mm fibre length is 50% or less, preferably 35% or less, more preferably 20% or less, most preferably 5% or less.

In one embodiment, the solid fraction of softwood of the lignocellulose material (3) comprises fine solid particles which are fiber-like or indefinable particles. The length weighted length Lc(l) of solid fraction is measured with Metso FS5. The length weighted Lc(l)fractions over 0.2 mm fibre length is 60% or less, preferably 45% or less, more preferably 30% or less, most preferably 15% or less.

In one embodiment, the lignocellulose particles are in the form of fiber sticks in the crude lignin, preferably also in the crude lignin slurry. In one embodiment, weight average particle size of the lignocellulose particle is below 1 mm, in one embodiment below 0.5 mm and in one embodiment below 300 µm.

In one embodiment, the crude lignin slurry is diluted with liquid, preferably with water, or steam to form the crude lignin feed to the separation stage. In one embodiment, feed concentration of the crude lignin slurry (5) is 2-60% by weight, preferably 5-40% by weight, more preferable 10-30% by weight, into a solid-liquid separation stage. If feed concentration of the crude lignin slurry is low so then size of the device increases. In one embodiment, the washing water which is recovered may be used in a dilution of the crude lignin slurry.

In one embodiment, the crude lignin slurry (5) is fed by pumping into the solid-liquid separation stage (6). In one embodiment, the crude lignin slurry (5) is fed by means of a pump, e.g. a mono pump or piston pump or other suitable pump, into the solid-liquid separation stage (6). Selection of the pump is based on e.g. feed concentration and/or viscosity of the crude lignin slurry. In one embodiment, the crude lignin slurry (5) is pumped, prepressed, washed and pressed.

The solid-liquid separation stage (6) may comprise one or more separation steps.

In one embodiment, the soluble carbohydrate containing fraction (10) is separated in one step. In one embodiment, the soluble carbohydrate containing fraction may be separated at the first step in two-step process or multi-step process. In one embodiment, the soluble carbohydrate containing fraction may be separated at the last step in two-step process or multi-step process. In one embodiment, the soluble carbohydrate containing fraction may be separated between the first and the last steps. Alternatively, the soluble carbohydrate containing fraction may be separated in more than one step. In one embodiment, the soluble carbohydrate containing fraction may be separated in each separation step. In one embodiment, a part of the soluble carbohydrates are separated in connection with the pretreatment and/or treatment processes in which the crude lignin or the crude lignin slurry is formed.

In one embodiment, the apparatus comprises one or more separation device. In one embodiment, the solid-liquid separation stage (6) comprises at least one separation device. In one embodiment, the solid-liquid separation stage comprises more than one separation device. In one embodiment, one or more separation steps can be done in the same separation device. In one embodiment, the separation device comprises one or more separation step, e.g. separation segment.

In one embodiment, the separation device is based on a countercurrent washing. In one embodiment, the separation device is selected from the group consisting of filtration device, centrifugal device and their combinations. In one embodiment, the separation device is selected from the group consisting of pressure filtration device, vacuum filtration device, filtration device based on underpressure, filtration device based on overpressure, filter press, other suitable press, centrifugal device and their combinations. In one embodiment, the separation device is a pressure filtration device, vacuum filtration device, filtration device based on underpressure or filtration device based on overpressure. Alternatively, the separation device can be another washing device in which low amount of washing water is used and washing is done in high dry matter content. Then good recovery can be achieved.

Preferably, the solid-liquid separation stage comprises the separation of the soluble carbohydrate containing fraction (10) from the crude lignin slurry (5). In one embodiment, the soluble carbohydrate containing fraction is separated from the crude lignin slurry by means of filtration, centrifugal treatment or their combinations. In one embodiment, the filtration is carried out by pressure, underpressure, vacuum or overpressure.

In the method of the invention, the solid-liquid separation stage (6) comprises a feeding, such as pumping, prepressing, washing and pressing wherein the soluble carbohydrate containing fraction (10) is separated from the crude lignin slurry (5). In one embodiment, the prepressing, washing and pressing are performed as one batch process. In one embodiment, the separation is performed by the filtration and the soluble carbohydrate containing fraction is separated in a liquid form and a solid cake is formed. Preferably, pressure is used in the filtration. In one embodiment, liquid is separated by a pressure difference, such as by means of vacuum or overpressure. In a preferred embodiment, the displacement washing of the crude lignin slurry (5) is carried out with small amount washing water in order to remove majority of sugars, inhibitors and other soluble compounds from the solid crude lignin material and to provide high recovery of soluble compounds. In one embodiment, the ratio of the washing water to solids or solid composition is 0.5:1-6:1 (w/w), preferably, 0.5:1-5:1 (w/w), more preferable 0.5:1-4:1 (w/w), most preferable 0.5:1-3:1 (w/w), in the washing. In one embodiment, the ratio of the washing water to solids or solid composition is 1:1-6:1 (w/w), preferably, 1:1-5:1 (w/w), more preferable 1:1-4:1 (w/w), most preferable 1:1-3:1 (w/w), in the washing. In this context washing water means any washing liquid or washing water. The washing water may be fresh washing water or recycled washing water. The washing water may be fresh water, drinking water, sugar containing liquid with low sugar content or other suitable liquid. In one embodiment, the filtration and washing is carried out in a static chamber, preferably in a non-moving chamber. In one embodiment, the filtration and washing is carried out in one device in the presence of pressure without mixing during the filtration and washing. Preferably, said separation device is in the vertical or horizontal plane or in the inclined plane. High concentration and recovery of the soluble material in the liquid phase can be achieved with small amount of washing water, and the pure solid fraction without soluble compounds can be achieved.

In one embodiment, the crude lignin slurry (5) is pumped to a separation device, such as a filter press. In one embodiment, the pressure of the pumping is maximal and the pressure level is achieved as fast as possible. In one embodiment, the pressure in the pumping is increased step by step or gradually. The steps of pressure may be different or similar. In one embodiment, the increase of the pressure comprises one or more steps. In one embodiment, the increase of the pressure comprises more than one step. In one embodiment, the control pressure of the pumping device is set directly to a set value, in one embodiment to 100%.

Figure 3:
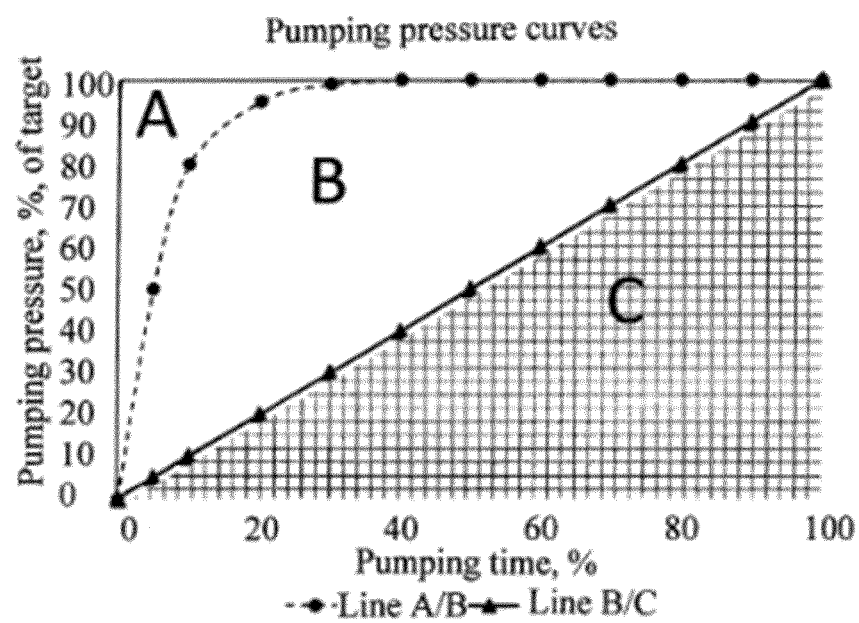
FIG. 3 shows pumping pressure curves.

In one embodiment, the pressure is increased with pumping procedure, where the pumping pressure is increased so that 80% or more of final pressure is achieved at the pumping time that is 10% or less of total pumping time (zone A in FIG. 3). Pumping time is the time when the liquid flow, e.g. filtrate, from the filter has slowed down to limit level of 5% or lower.

This limit level is defined as filtrate flow in minutes compared to total filtrate amount so far: end limit of pumping time=amount of filtrate in last minute/total filtrate amount.

In one embodiment, the crude lignin slurry (5) has good filtrating characteristics and thus pumping time with pumping procedure (zone A in FIG. 3) is short, e.g. equal or below 15 minutes.

In one embodiment, the crude lignin slurry (5) has moderate filtrating characteristics and thus pumping time by using pumping procedure zone A is long, e.g. above 15 minutes. To increase the flow rate, pumping procedure is changed to zone B or C (FIG. 3). In zone B pressure is increased so that less than 80% of final pressure is achieved at the pumping time that is 10% of total pumping time.

In one embodiment, the crude lignin slurry (5) has poor filtrating characteristics and thus pumping time with pumping procedure is high. To increase the flow rate, pumping pressure is increased so that the pumping pressure % is same or less than %-value of pumping time, in other words pumping pressure (%)=pumping time (%) (Y=X) or less (zone C in FIG. 3).

In the separation of the invention, the crude lignin slurry (5) is prepressed for preventing channeling in a cake of the crude lignin slurry during the separation and washing. In one embodiment, the prepressing is performed in the presence of pressure which is between 4-10 bar, or between 4.5-9 bar, or between 5-8 bar. Preferably, the pressure of the prepressing is similar or higher than pressure in the feeding, such as in the pumping. In one embodiment, the pressure of the prepressing is increased step by step or gradually. The steps of pressure may be different or similar. In one embodiment, the pressure is increased gradually so that max 70% of pressure is achieved at the pressing time that is 50% of total pressing time. Preferably, the pressure of the prepressing is kept during the washing. In one embodiment, pressure of the washing water is same or higher than pressure in a chamber of the separation device.

In one embodiment, the pressing is performed in the presence of pressure. In one embodiment, the pressure of the pressing is similar or higher than the pressure of the prepressing. In one embodiment, the pressure is between 5-20 bar, in one embodiment 6-18 bar, and in one embodiment 7-16 bar.

In one embodiment, the soluble carbohydrate containing fraction (10) is separated from the crude lignin slurry (5) by means of pressure filtration. In one embodiment, the apparatus comprises at least one pressure filtration device as the solid-liquid separation device. In one embodiment, the solid-liquid separation stage comprises one pressure filtration device. In one embodiment, the solid-liquid separation stage comprises more than one pressure filtration device. Preferably, the washing in the pressure filtration device is based on a displacement of liquid. In one embodiment, the pressure filtration comprises a pumping step, prepressing, washing step, pressing and removal of a cake. In the pumping step, the solid cake is formed and prepressed. Preferably, in the pumping step, a chamber of the pressure filtration device is filled, and prepressing is made. In one embodiment, air blow is made after the pumping step or after the first pressing step to further remove liquid from the cake. In one embodiment, the soluble carbohydrate containing fraction (10) is separated in connection with the pumping step. In the washing step, washing water is pressed through the cake and the cake is pressed and preferably dewatered. In the washing step, the liquid of the cake is displaced by water. In one embodiment, air blow is made in the washing step to further remove liquid from the cake. The washing water is separated by pressing in connection with the washing step. The dewatered solid cake is removed from the pressure filtrate device. Preferably, the dewatered solid cake forms a solid fraction (11). An advantage of the pressure filtration is that all separation steps can be carried out by one device.

In one embodiment, thickness of the cake is controlled so that liquid flow, amount of which is 1.0×mass of the dry cake, flows through the cake at the time that is below 60 min, preferably below 30 min, more preferably below 15 min and most preferably below 5 min. The washing water displaces the liquid in the cake.

In one embodiment, the soluble carbohydrate containing fraction (10) is separated from the crude lignin slurry (5) by means of a separation with at least two pressing steps. Preferably, the crude lignin slurry (5) is diluted between two pressing steps. In one embodiment, the separation is carried out so that the crude lignin slurry (5) is pressed, diluted and again pressed. In one embodiment, the apparatus comprises at least one solid-liquid separation device in which a soluble carbohydrate containing fraction (10) is separated from the crude lignin slurry (5) by at least two pressing steps and the crude lignin slurry is diluted between two pressing steps, and further the apparatus comprises at least one feeding device for feeding the crude lignin slurry (5) into the separation device, and means for supplying a solid fraction (11) and the soluble carbohydrate containing fraction (10) out from the separation device. In one embodiment, the dilution between two pressing steps is carried out in a separate vessel. In one embodiment, each pressing step is carried out in the presence of pressure, e.g. by a nip or in a pressure chamber or a pressurized chamber. In one embodiment, the pressing is carried out by means of a pressure filtration, e.g. in a filter press. In one embodiment, each pressing step is performed by means of similar or different pressing devices. In one embodiment, each pressing step is performed in the same separation device. In one embodiment, each pressing step is performed in separate separation devices.

In one embodiment, the soluble carbohydrate containing fraction (10) is separated from the crude lignin slurry (5) by means of a belt filtration. In one embodiment, the apparatus comprises at least one belt filtration device, such as a belt filter, as the solid-liquid separation device in which a soluble carbohydrate containing fraction (10) is separated from the crude lignin slurry (5) by filtration and washing. Further, the apparatus can comprise at least one feeding device for feeding the crude lignin slurry (5) into the belt filtration device, and means for supplying a solid fraction (11) and the soluble carbohydrate containing fraction (10) out from the belt filtration device. Preferably, the soluble carbohydrate containing fraction (10) is separated before the washing. In one embodiment, the soluble carbohydrate containing fraction (10) is separated by vacuum before the washing. In one embodiment, the belt filtration is based on a countercurrent washing. In one embodiment, washing water can be removed by means of vacuum during the washing. In one embodiment, fresh washing water, such as water or liquid, is introduced to the belt filtration device, preferably in an end part of the belt filtration device. In one embodiment, at least a part of the washing water, such as water or liquid, is recirculated to a previous separation step, e.g. segment, of the belt filtration device. In one embodiment, at least a part of the washing water is recirculated back to a previous separation step, e.g. segment, from each separation step in the belt filtration device. In one embodiment, at least a part of the washing water is recirculated continuously. An amount of washing water can be decreased by means of the recirculation. In one embodiment, the belt filtration separation comprises at least one pressing stage.

In one embodiment, the belt filtration device is a twin-wire press. In one embodiment, the separation is carried out in the presence of overpressure in the twin-wire press.

In one embodiment, the solid-liquid separation is carried out in one or more separation steps in the separation stage. In one embodiment, the solid-liquid separation stage comprises more than one sequential separation steps. In one embodiment, the solid-liquid separation stage comprises different procedures which may be done in separation steps. Alternatively, more than one procedure is done in one process step.

In one embodiment, the separation is carried out in below 10 steps, or below 4 steps, or below 3 steps. In one embodiment, washing water is fed in stages. In one embodiment, the washing is done in stages, and the pressure is increased between each steps. In one embodiment, the washing is done in stages, and air blow is made after each step.

In one embodiment, the method of the invention comprises more than one separation stages. In one embodiment, the method comprises more than one sequential separation stages. In different separation stages the separation can be carried out by means of similar or different separation methods or separation devices.

In one embodiment, the soluble carbohydrate containing fraction (10) is monomerized.

In one embodiment, the soluble carbohydrate containing fraction (10) comprises soluble C6 carbohydrates, such as $C_6H_{12}O_6$ or $C_6(H_2O)_n$, and other soluble carbohydrates, lignin and some other compounds. The soluble carbohydrate containing fraction may contain also C5 carbohydrates. Preferably, the soluble carbohydrate containing fraction can contain monosaccharides, and oligosaccharides. Further, the soluble carbohydrate containing fraction can contain also polysaccharides. In one embodiment, the soluble carbohydrate containing fraction contains galactose, glucose, mannose, arabinose, xylose, glucuronic acid and galacturonic acid. Total carbohydrate content can be measured with HPLC after acid hydrolysis according to standard SCAN-CM 71:09. Monomeric carbohydrate content can be measured with HPLC from liquid fraction directly without acid hydrolysis. In one embodiment, the total soluble concentrate of the soluble carbohydrate containing fraction is between 20 to 280 g/l, preferably between 40 to 240 g/l, more preferable between 55 to 210 g/l after the solid-liquid separation. In one embodiment, the total soluble concentrate of the soluble carbohydrate containing fraction is between 10 to 210 g/l, preferably between 20 to 180 g/l, more preferable between 30 to 140 g/l after the solid-liquid separation. In one embodiment, the total soluble concentrate of the soluble carbohydrate containing fraction is between 30 to 230 g/l, preferably between 50 to 220 g/l, more preferable between 100 to 210 g/l after the solid-liquid separation. Preferably, the soluble carbohydrate containing fraction is in the form of solution. In one embodiment, carbohydrate concentrate of the soluble carbohydrate containing fraction is between 20 to 200 g/l, preferably between 40 to 170 g/l, more preferable between 50 to 150 g/l after the solid-liquid separation. In one embodiment, carbohydrate concentrate of the soluble carbohydrate containing fraction is between 10 to 150 g/l, preferably between 20 to 125 g/l, more preferable between 30 to 100 g/l after the solid-liquid separation. In one embodiment, carbohydrate concentrate of the soluble carbohydrate containing fraction is between 25 to 230 g/l, preferably between 50 to 215 g/l, more preferable between 100 to 200 g/l after the solid-liquid separation.

Preferably, at least a part of the soluble carbohydrate containing fraction is supplied out from the separation stage. The soluble carbohydrate containing fraction can be supplied out after any desired step of the separation stage. In one embodiment, the soluble carbohydrate containing fraction is supplied out after the first step of the separation stage.

The soluble carbohydrate containing fraction (10) can be recovered. The soluble carbohydrate containing fraction may be used as component in manufacturing a final product. The soluble carbohydrate containing fractions can be concentrated for further use. In one embodiment, the monomerization of the soluble carbohydrate containing fraction is made before the further processing. In one embodiment, the soluble carbohydrate containing fraction is supplied to a fermentation process. In one embodiment, the soluble carbohydrate containing fraction is used as a source material in fermentation. In one embodiment, the soluble carbohydrate containing fraction is supplied to a hydrolysis process. In one embodiment, the soluble carbohydrate containing fraction is used as a source material in hydrolysis, such as by acid hydrolysis, enzymatic hydrolysis or the like. In one embodiment, the soluble carbohydrate containing fraction is supplied to a catalytic treatment process. In one embodiment, the soluble carbohydrate containing fraction is used as a source material in the catalytic process. In one embodiment, the soluble carbohydrate containing fraction is supplied to a polymerization process. In one embodiment, the soluble carbohydrate containing fraction is used as a source material in the polymerization. In one embodiment, the soluble carbohydrate containing fraction is supplied to an enzymatic process. In one embodiment, the soluble carbohydrate containing fraction is used as a source material in the enzymatic treatment. In one embodiment, the soluble carbohydrate containing fraction is supplied to a manufacture of binder. In one embodiment, the soluble carbohydrate containing fraction is used as a source material in the manufacture of binder, e.g. wood based binder. In one embodiment, the soluble carbohydrate containing fraction is supplied to a manufacture of food. In one embodiment, the soluble carbohydrate containing fraction is used as a source material in the manufacture of food. In one embodiment, the soluble carbohydrate containing fraction is supplied to a manufacture of feed. In one embodiment, the soluble carbohydrate containing fraction is used as a source material in the manufacture of feed. The soluble carbohydrate containing fraction may be supplied directly to a fermentation, hydrolysis, catalytic treatment process, polymerization process, enzymatic process, manufacture of binder, manufacture of feed, manufacture of food, or other suitable process, or alternatively via a suitable treatment step or an additional step, e.g. additional concentration step or purification step, to a fermentation, hydrolysis, catalytic treatment process, polymerization process, manufacture of binder, manufacture of feed, manufacture of food, or other suitable process, e.g. enzymatic process.

In one embodiment, a solid fraction (11) comprising solids is supplied out from the solid-liquid separation stage. In one embodiment, the solid fraction (11) comprises lignin and solid C6 carbohydrates, such as ($C_6H_{12}O_6$ or $(C_6H_2O)_n$), other solid carbohydrates and other solid components, and some other compounds, such as some residual soluble material. In one embodiment, the solid fraction is in the form of a cake.

In one embodiment, dry matter content of the solid fraction (11) of the crude lignin is 20-80% by weight. In one embodiment, dry matter content of the solid fraction is 30-60% by weight, preferably 40-60% by weight, more preferably 45-55% by weight, after the solid-liquid separation stage. In one embodiment, dry matter content of the solid fraction is 7-70% by weight, preferably 15-45% by weight, more preferably 30-40% by weight, after the solid-liquid separation stage. The dry matter content is determined at 60° C. by means of evaporating. In one embodiment, the determination of the dry matter content may be done so that it is based, at least partly or as applied, on NREL (National renewable energy laboratory) Laboratory Analytical Procedures for standard biomass analysis determined in the Technical Report NREL/TR-510-48087 (revised July 2011).

In one embodiment, the cellulose content, i.e. glucan content, of the solid fraction (11) of the crude lignin is 3-70% by weight, preferably 5-60% by weight and more preferably 10-60% by weight, analyzed as glucose.

In one embodiment, the carbohydrate content of the solid fraction (11) of the crude lignin is between 2 to 50%. In one embodiment, the carbohydrate content is 10-30%, and more preferably 15-25%. In one embodiment, the carbohydrate content is 40-70%, and more preferably 40-60%. In one embodiment, the carbohydrate content is 5-80%, and more preferably 40-70%.

In one embodiment, the solid fraction contains soluble compounds below 15%, preferably below 5%, more preferably below 3% by weight, after the solid-liquid separation stage. In one embodiment, water soluble matter is determined by a gravimetric washing method. The determination by the gravimetric washing method may be done as following: dry matter content (DM %) of raw material, e.g. the solid and soluble fraction, is measured at 60° C., the amount of solids remaining after heating the sample at 60° C. to constant weight is measured and dry matter content is calculated based on wet and dry weights. For washing about 10 g bone dry of the wet material under investigation is taken, weighted (exact weighed amount) and mixed with hot water (50° C.) in a vessel so that total amount is 200 g, the mixture is mixed 20 s (Bamix Mono freehand food blender, 'C' blade, speed 1 (7000 rpm)), the mixture is soaked with soaking time 5 min, the mixture is mixed 10 s (Bamix Mono freehand food blender, C' blade, speed 1 (7000 rpm)), mass of a dry filter paper is measured, the mixture is filtered by means of Büchner (dia.125 mm) and the filter paper, an inward relief valve is closed when a cake is matt (dry) in whole, a filtrate is taken and the blender and vessel is washed with the filtrate and the filtrate is filtered again through the cake, the cake is washed three times with hot water, a 100 g, so that suction effect is maintained the whole time and washing water (100 g) is added when the cake is matt (dry) in whole, a foil dish is weighed, the cake with the filter paper is dried in the foil dish, the dried cake (60° C.) with the filter paper is weighed in the foil dish and mass of the filter paper and foil dish is subtracted from mass of the dried cake, filter paper and foil dish, and then soluble matter free solid, i.e. water insoluble solids (WIS) of wet material under investigation, can be determined. Water insoluble solids, WIS %, can be calculated: WIS %=(weight of washed and dried material, e.g. the cake)/(weight of the wet slurry for washing, e.g. the raw material). Water soluble matter, WS %, of dry matter can be calculated: WS %=(dry matter (DM %) of the original slurry, e.g. the raw material)−(water insoluble solids, WIS %).

In one embodiment, particle size of the solid particles in the crude lignin cake (11) is determined by an optical measurement Metso FS5 and by a laser diffraction method Coulter LS230. The determination of particle size of the solid particles in the crude lignin cake (11) needs proper sample preparation to disperse single particles to water. For dispersing about 10 g bone dry of the wet material under investigation is taken and mixed with water (about 20° C.) in a vessel so that total amount is 200 g, the mixture is soaked with soaking time 15 min, and the mixture is mixed 60 s (Bamix Mono freehand food blender, 'C' blade, speed 1 (7000 rpm)). After that the material is ready to determination specific preparation.

In one embodiment, the solid fraction of the crude lignin (11) comprises solid particles which are fiber-like or indefinable particles with longest dimension shorter than 0.2 mm measured with optical Metso FS5 (fraction F1(l) of length weighted Lc(l) measurements and calculations). In one embodiment, the solid fraction of the crude lignin comprises particles with longest dimension shorter than 0.2 mm over 70% (F1(l)>70%), preferably over 80%, more preferably over 90% and most preferably over 98% by weight, defined by Metso FS5.

In one embodiment, the solid fraction of the crude lignin (11) comprises solid particles which are fiber-like or indefinable particles measured in water solution with a laser diffraction method Coulter LS230. In one embodiment, the solid fraction of the crude lignin comprises particles with equivalent circular area diameter smaller than 50 μm over 50%, preferably over 70%, more preferably over 90% and most preferably over 98% by weight, defined by Coulter LS230.

In one embodiment, the solid fraction of the crude lignin (11) comprises solid particles which are fiber-like or indefinable particles measured in water solution with a laser diffraction method Coulter LS230, PIDS (Polarization Intensity Differential Scattering) including. In one embodiment, the solid fraction of the crude lignin comprises particles with median equivalent circular area diameter less than 50 μm, preferably less than 40 μm, more preferably less than 30% and most preferably less than 20 μm, defined by Coulter LS230.

Coulter LS230 is based on a laser diffraction, and it measures particle size distributions by measuring the pattern of light scattered by the constituent particles in the sample. Coulter LS230 comprises an optical module consisting of a diffraction component and PIDS (Polarization Intensity Differential Scattering) assembly. The measuring range is 0.04-2000 μm so that the measuring range is 0.4-2000 μm with the diffraction component and the measuring range is 0.04-0.4 μm with the PIDS assembly.

In one embodiment, a solid fraction (11) comprising solids (11) is recovered. In one embodiment, the solid fraction is supplied to a hydrolysis which may be selected from the group consisting of acid hydrolysis, enzymatic hydrolysis, supercritical hydrolysis and/or subcritical hydrolysis and their combinations, or a polymerization process or to a manufacture of a composite material or to a manufacture of binder, e.g. wood based binder, or to a manufacture of feed, or to a manufacture of food or a combustion process or other suitable process or their combinations. The solid fraction may be supplied directly to a hydrolysis, polymerization process, manufacture of a composite material, manufacture of binder, manufacture of feed, manufacture of food, combustion process or other suitable process, or alternatively via a suitable treatment step or an additional step, e.g. additional concentration step or purification step, to a hydrolysis, polymerization process, manufacture of a composite material, manufacture of binder, manufacture of feed, manufacture of food, combustion process or other suitable process.

The method according to the present invention provides the soluble carbohydrate containing fraction and solid fraction with high concentration and with good quality. The solid fraction has very high concentration of lignin and glucan and its hydrated products. Further, the solid fraction has very high purity.

The present invention provides an industrially applicable, simple and affordable way of making the pure solid fraction and further the soluble carbohydrate containing fraction. The method according to the present invention is easy and simple to realize as a production process. The method according to the present invention is suitable for use in the manufacture of the different lignin based fractions and final products from different starting materials.

EXAMPLES

The invention is described in more detail by the following examples with reference to accompanying drawings.

Example 1

In this example a soluble carbohydrate containing fraction is produced according to a process of FIG. 2.

The lignocellulose material (3) is formed from plant based raw material (1) by means of pretreatment (2). Soluble components may be removed from the lignocellulose material. The lignocellulose material (3) is further processed by means of an enzymatic treatment or an acid treatment (4) in order to form crude lignin slurry (5).

The crude lignin slurry (5) is fed into a solid-liquid separation stage (6) comprising a pressure filtration device in which a soluble carbohydrate containing fraction (10) is separated from the crude lignin slurry (5) by pumping, filtrating and using displacement washing and in which the crude lignin slurry (5) is pumped, prepressed, washed and pressed. Optionally, after that air blowing is made. A soluble carbohydrate containing fraction (10) containing soluble C6 carbohydrates is separated from the crude lignin slurry in the pumping and prepressing step of the pressure filtration. A washing water is removed by pressing from a solid cake of the solid fraction (11) in the washing step of the pressure filtration. A solid fraction (11) containing e.g. solids, such as lignin, solid carbohydrates, and some soluble sugar, oligomer and polymer residual is removed from the pressure filtration device.

Example 2

In this example a liquid and solid fraction is produced.

Birch wood chips were pretreated in two-step dilute acid steam explosion process to dissolve hemicellulose and to create soluble carbohydrate containing composition. Portion of this soluble carbohydrate containing composition is removed before rapid pressure release of lignocellulose material in the steam explosion.

The solid material was put to reactor and diluted to suitable dry matter content to hydrolyze most of the cellulose and hemicellulose. The crude lignin slurry was formed in hydrolyzing step. After hydrolyzing for certain period of time solid-liquid separation was done with pressure filter as described in Table 1. Washing water pressure was same or higher than pressure in chamber. Results are shown in Table 2.

TABLE 1

| | | |
|---|---|---|
| Dry matter content of crude lignin slurry for filter press | % | 20 |
| Temperature of crude lignin slurry for filter press | ° C. | 50 |
| Feeding and first press | | |
| Feeding time | min | 7 |
| Maximum pressure in feeding | bar | 6 |
| Maximum pressing pressure 1 | bar | 6 |
| Pressing time | min | 2 |
| Pumping pressure in washing 6-7 bar | | |
| Wash water temperature | ° C. | 50 |
| Amount of washing water | l | 4 |
| Amount of washing water, liquid to solid ratio | L:S | 1.9 |
| Washing time | min | 8 |
| Pressing pressure | bar | 12 |
| Pressing time | min | 2 |
| Air blowing | | |
| Blowing time | min | 2 |
| Cake properties | | |
| Cake wet thickness | mm | 32 |
| Dry matter content of cake | % | 57.3 |

TABLE 2

| Pressure filtration | Only pressing | Pressing + washing 1.9:1 |
|---|---|---|
| Dry matter, % | 58.8 | 59.3 |
| Water insoluble solids, % | 51.9 | 56.6 |
| Water soluble matter of dry matter, % | 11.6% | 4.5 |

Example 3

In this example, two samples of crude lignin were prepared by hydrolyzing majority of cellulose of lignocellulose material to soluble form. Cellulose of pretreated wood based lignocellulose material was enzymatically hydrolyzed to form crude lignin sample 1.

Cellulose of pretreated wood based lignocellulose material was hydrolyzed to form crude lignin sample 2. Particle size of the solid particles in the crude lignin cake (11) of two different crude lignin samples are determined by an optical measurement Metso FS5 and by a laser diffraction method Coulter LS230, PIDS including. Also chemical composition of the samples is measured. The crude lignin samples were dispersed to water for particle size measurements. Results are shown in Table 3.

TABLE 3

| Property | Unit | Method | Solid fraction of crude lignin 1 | Solid fraction of crude lignin 2 |
|---|---|---|---|---|
| Acid-insoluble lignin, grav. | % | T-222 | 66.8 | 49.3 |
| Acid-soluble lignin, UV 205 | % | T-UM 250 | 1.8 | 1.7 |
| Arabinose, acid hydrolysis, HPAE-PAD | mg/g | SCAN-1 CM7 | 0.0 | 0.0 |

TABLE 3-continued

| Property | Unit | Method | Solid fraction of crude lignin 1 | Solid fraction of crude lignin 2 |
|---|---|---|---|---|
| Rhamnose, acid hydrolysis, HPAE-PAD | mg/g | SCAN-CM71 | 0.0 | 0.0 |
| Galactose, acid hydrolysis, HPAE-PAD | mg/g | SCAN-CM71 | 0.0 | 0.0 |
| Glucose, acid hydrolysis, HPAE-PAD | mg/g | SCAN-CM71 | 250.8 | 507.1 |
| Xylose, acid hydrolysis, HPAE-PAD | mg/g | SCAN-CM71 | 10.9 | 0.0 |
| Mannose, acid hydrolysis, HPAE-PAD | mg/g | SCAN-CM71 | 2.0 | 0.0 |
| Carbohydrates, acid hydrolysis, HPAE-PAD, total | mg/g | SCAN-CM71 | 263.7 | 507.1 |
| FS5 Length weighted fiber length Lc(1) ISO | mm | Determined by Metso FS5 based on ISO 16065-N or TAPPI T271 | 0.651 | 0.589 |
| FS5 Fiber width | µm | | 21.6 | 9.5 |
| FS5 Fines | % | | 99.82 | 98.05 |
| FS5 Fines (Flakes) | % | | 97.62 | 85.05 |
| Population based particle length Lc(n) | mm | | 0.018 | 0.016 |
| Length weighted particle length Lc(1) | mm | | 0.023 | 0.034 |
| Weight weighted particle length Lc(w) | mm | | 0.045 | 0.14 |
| FS5 Fiber fractions 0-0.2 mm | % | | 99.82 | 98.05 |
| FS5 Fiber fractions 0.2-0.6 mm | % | | 0.13 | 1.29 |
| FS5 Fiber fractions 0.6-1.2 mm | % | | 0.02 | 0.13 |
| FS5 Fiber fractions 1.2-2.0 mm | % | | 0.0 | 0.52 |
| FS5 Fiber fractions 2.0-3.2 mm | % | | 0.03 | 0.0 |
| FS5 Fiber fractions 3.2-7.6 mm | % | | 0.0 | 0.0 |
| Particle width of fraction 0-0.2 mm | µm | | 3.53 | 4.25 |
| Particle width of fraction 0.2-0.6 mm | µm | | 25.20 | 6.10 |
| Coulter LS Particle size Mean | µm | | 14.99 | 7.115 |
| Coulter LS Particle size Median | µm | | 11.62 | 4.360 |
| Coulter LS Particle size Mode | µm | | 13.61 | 18.000 |
| Coulter LS Particle size <75 µm | % | | 100 | 100 |
| Coulter LS Particle size <50 µm | % | | 99.5 | 100 |
| Coulter LS Particle size <25 µm | % | | 80.8 | 99.9 |
| Coulter LS Particle size <10 µm | % | | 43.8 | 71.50 |
| Coulter LS Particle size <5 µm | % | | 21.2 | 54.00 |
| Coulter LS Particle size <2 µm | % | | 5.66 | 24.80 |
| Coulter LS Particle size <1 µm | % | | 1.25 | 7.30 |
| Coulter LS Particle size <0.5 µm | % | | 0.63 | 1.45 |

Example 4

In this example crude lignin slurry was pumped to a filter press. The filter press had total filtrating area of 0.81 m² in three filtrating chambers and water removal is two-sided in each chamber.

The pressure of the pumping was 5.6 bar at maximum and the pressure level was increased gradually so that about 80% of final pressure was achieved at the pumping time of 30 seconds. Filtrate flowing out was collected and weighted and results can be seen in Table 4. Pumping time is the time when the filtrate flow from the filter has slowed down to limit level of 5% or lower. In this case the pumping time was 7 minutes.

TABLE 4

| Pumping time, mm:ss | Cumulative filtrate mass flown out, kg | Amount of filtrate flown out during last minute/total filtrate amount at this point |
|---|---|---|
| 2:00 | 8.5 | |
| 3:00 | 10.6 | 20% |
| 4:00 | 12.2 | 14% |
| 5:00 | 13.7 | 11% |
| 6:00 | 14.9 | 8% |
| 7:00 | 15.7 | 5% |

Example 5

Figure 4:
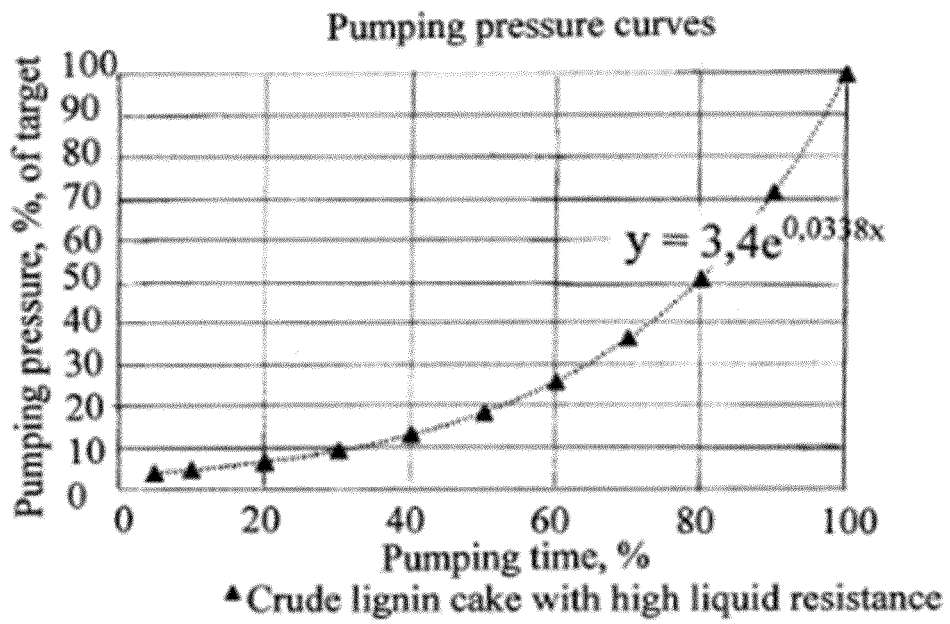
FIG. 4 shows pressure of the pumping in one example carried out according to one method embodiment of the present invention.

In this example crude lignin slurry was pumped to a filter press. The water flow resistance of formed cake was high and thus the pumping time was long. The pressure of the pumping was set to maximum in the end of pumping time and the pressure level was increased gradually based on following formula: pumping pressure=$3.4e^{0.0338*x}$, where x is pumping time (FIG. 4). Low pumping pressure in the beginning let particles of crude lignin suspension settle to filtration chamber evenly, which makes homogenous filter cake structure possible and thus liquid flow through cake can be increased compared to case where pumping pressure is 80% or higher in pumping time of 10%.

Example 6

Figure 5:
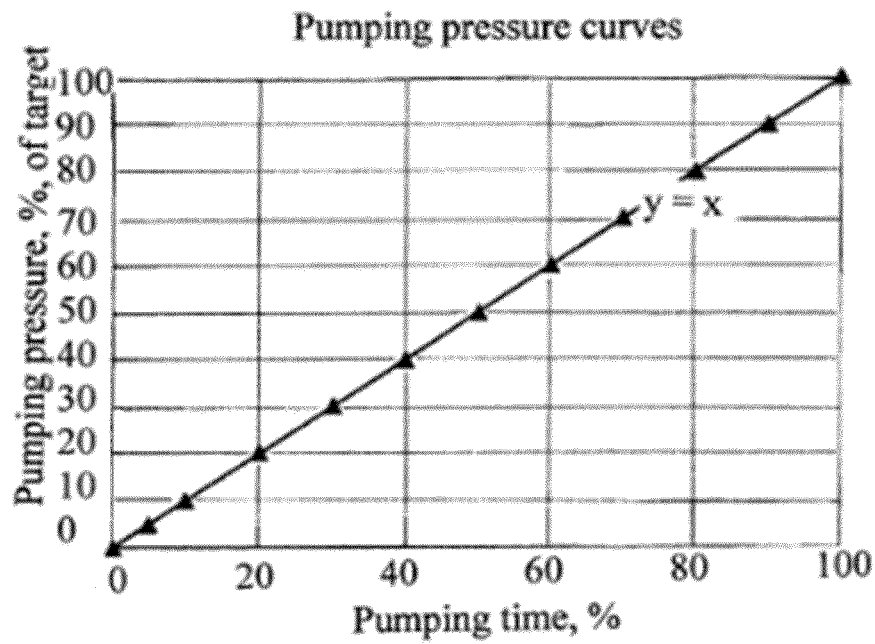
FIG. 5 shows pressure of the pumping in one example carried out according to one method embodiment of the present invention.

In this example crude lignin slurry was pumped to a filter press. The water flow resistance of formed cake was high and thus the pumping time was long. The pressure of the pumping was set to maximum in the end of pumping time and the pressure level was increased linear based on following formula: pumping pressure %=pumping time % (FIG. 5). Low pumping pressure in the beginning let particles of crude lignin suspension settle to filtration chamber evenly, which makes homogenous filter cake structure possible and thus liquid flow through cake can be increased compared to case where pumping pressure is 80% or higher in pumping time of 10%.

Example 7

In this example a liquid and solid fraction is produced.
Birch wood chips were pretreated in two-step dilute acid steam explosion process to dissolve hemicellulose and to create soluble carbohydrate containing composition. Portion of this soluble carbohydrate containing composition is removed before rapid pressure release of lignocellulose material in the steam explosion.

The solid lignocellulose material was put to reactor and diluted to suitable dry matter content to hydrolyze most of the cellulose and hemicellulose. The crude lignin slurry was formed in hydrolyzing step. After hydrolyzing for certain period of time solid-liquid separation was done with pressure filter as described in the Table 5. The filter press has filtrating area of 0.1 m² in one filtrating chamber and water removal is to one direction of the chamber.

After pumping the crude lignin slurry to filter press, the formed cake was pressed only once in case of trial 1 and also prepressed in case of trial 2. The prepressing pressure in trial 2 was 8 bar and the pressure level was decreased before washing down to 5 bar. The pressure of washing water pumped to the cake was 5.5 bar. Results are shown in Table 6.

TABLE 5

| | | |
|---|---|---|
| Dry matter content of crude lignin slurry for filter press | % | 17 |
| Temperature of crude lignin slurry for filter press | ° C. | 45 |

| | | Trial 1 | Trial 2 |
|---|---|---|---|
| Feeding and first press | | | |
| Feeding time | min | 3 | 3 |
| Pressure in feeding | bar | 5 | 5 |
| Prepressing pressure | bar | — | 8 |
| Prepressing time | min | — | 3:10 |
| Wash water temperature | ° C. | — | 50 |
| Amount of washing water, liquid to solid ratio | L:S | — | 3 |
| Washing time | min | — | 2 |
| Pressing pressure in final pressing | bar | 16 | 16 |
| Pressing time | min | 3:15 | 2:30 |
| Air blowing time | min | 1:30 | 1:30 |
| Weight of wet cake | kg | 1.0 | 0.9 |

TABLE 6

| Pressure filtration | Only pressing | Pressing + washing 3:1 |
|---|---|---|
| Dry matter, % | 52.2 | 53.5 |
| Water insoluble solids, % | 45.7 | 52.2 |
| Water soluble matter of dry matter, % | 12.4 | 2.5 |

The method according to the present invention is suitable in different embodiments to be used for producing the most different kinds of solid lignin fractions and also soluble carbohydrate containing fractions from different raw materials.

The invention is not limited merely to the example referred to above; instead many variations are possible within the scope of the inventive idea defined by the claims.

The invention claimed is:

1. A method for washing a crude lignin slurry, wherein the method comprises:
   forming a crude lignin slurry by processing lignocellulose material formed from plant based raw material using enzymatic hydrolysis;
   feeding the crude lignin slurry to at least one solid-liquid separation stage comprising at least one pressure filtration device;
   separating a soluble carbohydrate containing fraction from the crude lignin slurry using displacement washing in the pressure filtration device, the displacement washing including prepressing, washing, and pressing of the crude lignin slurry in connection with the separation of the soluble carbohydrate containing fraction from the crude lignin slurry, the ratio of the washing water to solids in the displacement washing being 0.5:1-6:1 (w/w) and the pressure being kept during the washing; and
   recovering a solid fraction and the soluble carbohydrate containing fraction.

2. The method according to claim 1, wherein the hydrolysis is a cellulose hydrolysis.

3. The method according to claim 1, wherein the crude lignin slurry has been further processed via an acid treatment.

4. The method according to claim 1, wherein the soluble carbohydrate containing fraction is separated from the crude lignin slurry using filtration, centrifugal treatment or their combinations.

5. The method according to claim 1, wherein the solid-liquid separation stage comprises a filtration in which the filtration is carried out by pressure or overpressure.

6. The method according to claim 1, wherein the pressure is increased step by step or gradually in the feeding to the solid-liquid separation stage.

7. The method according to claim 1, wherein the prepressing is performed in the presence of pressure which is between 4-10 bar.

8. The method according to claim 1, wherein the pressure of the prepressing is similar or higher than pressure in the feeding.

9. The method according to claim 1, wherein the pressure of the pressing is similar or higher than the pressure of the prepressing.

10. The method according to claim 1, wherein the total soluble concentrate of the soluble carbohydrate containing fraction is between 20 to 280 g/l.

11. The method according to claim 1, wherein dry matter content of the solid fraction is 30-60% by weight.

12. The method according to claim 1, wherein the solid-liquid separation stage comprises more than one separation steps.

13. The method according to claim 1, wherein the plant based raw material is wood based material or a mixture comprising wood based material.

14. The method of claim 1, wherein a soluble carbohydrate containing fraction is obtained.

15. The method of claim 1, wherein the solid fraction is obtained.

16. The method of claim 14, wherein the soluble carbohydrate containing fraction is usable as a source material in fermentation, hydrolysis, catalytic process, polymerization process, enzymatic process, manufacture of binder, manufacture of feed, manufacture of food or their combination.

17. The method of claim 15, wherein the solid fraction is usable as a source material in hydrolysis, polymerization process, manufacture of a composite material, manufacture of binder, manufacture of feed, manufacture of food, combustion process or their combination.

* * * * *